United States Patent
Gray et al.

(10) Patent No.: US 11,890,231 B2
(45) Date of Patent: Feb. 6, 2024

(54) DIGITALLY RECONSTRUCTING LASER CUTTING PATTERNS IN OPHTHALMIC SURGICAL LASER SYSTEM

(71) Applicant: AMO Development, LLC, Irvine, CA (US)

(72) Inventors: Paul Gray, San Jose, CA (US); Guangming Dai, Fremont, CA (US); Alireza Malek Tabrizi, Fremont, CA (US); Hong Fu, Pleasanton, CA (US)

(73) Assignee: AMO Development, LLC, Irvine, CA (US)

( * ) Notice: Subject to any disclaimer, the term of this patent is extended or adjusted under 35 U.S.C. 154(b) by 675 days.

(21) Appl. No.: 17/102,431

(22) Filed: Nov. 23, 2020

(65) Prior Publication Data

US 2021/0196518 A1 Jul. 1, 2021

Related U.S. Application Data

(63) Continuation of application No. 62/955,225, filed on Dec. 30, 2019.

(51) Int. Cl.
*A61F 9/008* (2006.01)
*A61F 9/007* (2006.01)
*G06F 30/23* (2020.01)

(52) U.S. Cl.
CPC ...... *A61F 9/00814* (2013.01); *A61F 9/00763* (2013.01); *G06F 30/23* (2020.01); *A61F 2009/00844* (2013.01)

(58) Field of Classification Search
CPC .............. A61F 9/008; A61F 2009/00897
See application file for complete search history.

(56) References Cited

U.S. PATENT DOCUMENTS

| 9,411,938 B2 | 8/2016 | Rathjen |
| 9,855,170 B2 | 1/2018 | Bischoff et al. |

(Continued)

FOREIGN PATENT DOCUMENTS

| WO | 2012076032 A1 | 6/2012 | |
| WO | WO-2012076032 A1 * | 6/2012 | ......... A61F 9/00763 |

OTHER PUBLICATIONS

English translation of WO 2012/076032 A1 published on Jun. 14, 2012 (Year: 2012).*

*Primary Examiner* — Allen Porter
*Assistant Examiner* — Adreanne A. Arnold
(74) *Attorney, Agent, or Firm* — Johnson & Johnson Surgical Vision, Inc.

(57) ABSTRACT

An ophthalmic surgical laser system includes a laser beam delivery system having multiple moving components for scanning a laser focal spot in a target eye tissue, where the motors that actuate some of the moving components are equipped with respective digital encoders that measure actual motor positions. A controller controls the laser beam delivery system to perform a treatment scan, while recording the actual motor positions from the encoders. Using the actual motor positions and a calibration relationship between actual motor positions and delivered laser focal spot positions in a target tissue, a laser cutting pattern is digitally reconstructed, which represents the incisions actually achieved by the treatment scan. The reconstructed laser cutting pattern may be visually inspected and further analyzed, e.g. to compare it to the intended laser cutting pattern used to execute the treatment scan, to calculate the achieved refractive correction, or to simulate tissue resetting.

17 Claims, 8 Drawing Sheets

(56) References Cited

U.S. PATENT DOCUMENTS

| | | |
|---|---|---|
| 9,918,873 B2 | 3/2018 | Woodley et al. |
| 9,962,292 B2 | 5/2018 | Bergt et al. |
| 10,105,261 B2 | 10/2018 | Simoneau et al. |
| 10,369,052 B2 | 8/2019 | Fu |
| 10,779,988 B2 | 9/2020 | Fu et al. |
| 2008/0033408 A1 | 2/2008 | Bueler et al. |
| 2012/0150156 A1* | 6/2012 | Wolfel .............. A61F 9/008 |
| | | 606/4 |
| 2018/0028355 A1 | 2/2018 | Raksi |
| 2020/0064622 A1 | 2/2020 | Rahaman et al. |

* cited by examiner

DIGITALLY RECONSTRUCTING LASER CUTTING PATTERNS IN OPHTHALMIC SURGICAL LASER SYSTEM

CROSS-REFERENCE TO RELATED APPLICATIONS

This application claims the benefit under 35 U.S.C. § 119(e) of U.S. Provisional Patent Application No. 62/955,225, filed Dec. 30, 2019, which is incorporated herein by reference in its entirety.

BACKGROUND OF THE INVENTION

Field of the Invention

This invention relate generally to laser-assisted ophthalmic surgery, and more particularly, to systems and methods implemented in an ophthalmic surgical laser system for digitally reconstructing, inspecting, and analyzing laser cutting patterns.

Description of Related Art

Vision impairments such as myopia (near-sightedness), hyperopia and astigmatism can be corrected using eyeglasses or contact lenses. Alternatively, the cornea of the eye can be reshaped surgically to provide the needed optical correction. Eye surgery has become commonplace with some patients pursuing it as an elective procedure to avoid using contact lenses or glasses to correct refractive problems, and others pursuing it to correct adverse conditions such as cataracts. With recent developments in laser technology, laser surgery is becoming the technique of choice for ophthalmic procedures.

Different laser eye surgical systems use different types of laser beams for the various procedures and indications. These include, for instance, ultraviolet lasers, infrared lasers, and near-infrared, ultra-short pulsed lasers. Ultra-short pulsed lasers emit radiation with pulse durations as short as 10 femtoseconds and as long as 3 nanoseconds, and a wavelength between 300 nm and 3000 nm.

To form an incision in a target eye tissue, the focal spot of the pulsed laser beam is delivered to the target eye tissue by an optical scanning system, where they interact with the eye tissue to form cavities (bubbles) in the tissue. By scanning the laser focal spot according to predefined scan patterns, the overlapping or closely adjacent bubbles form incisions (cuts) having defined two-dimensional shapes. The term "scan" or "scanning" refers to the movement of the laser focal spot along a desired path or in a desired pattern.

Prior surgical approaches for reshaping the cornea include laser assisted in situ keratomileusis ("LASIK"), photorefractive keratectomy ("PRK") and Small Incision Lens Extraction ("SmILE"). In a LASIK procedure, an ultra-short pulsed laser is used to cut a corneal flap to expose the corneal stroma for photoablation using ultraviolet beams from an excimer laser. Photoablation of the corneal stroma reshapes the cornea and corrects the refractive condition such as myopia, hyperopia, astigmatism, and the like. In a PRK procedure where no flap is created, the epithelium layer is first removed, and some stroma material is then removed by an excimer laser. The epithelium layer will grow back within a few days after the procedure. A SmILE procedure involves tissue removal using two femtosecond laser incisions that intersect to create a lenticule shaped tissue which is then extracted. The extraction of the lenticule changes the shape of the cornea and its optical power to accomplish vision correction. Lenticular extractions can be performed either with or without the creation of a corneal flap. With the flapless procedure, a refractive lenticule is created in the intact portion of the anterior cornea and removed through a small incision.

SUMMARY OF THE INVENTION

Embodiments of the present invention provide a method and related apparatus, implemented in an ophthalmic surgical laser system, for digitally reconstructing, inspecting, and analyzing laser cutting patterns.

In one aspect, embodiments of the present invention provides an ophthalmic surgical laser system which includes: a laser source configured to generate a pulsed laser beam; a laser beam delivery system configured to deliver a laser focal spot of the laser beam to a target tissue of a patient's eye, the laser beam delivery system including a plurality of optical elements each configured to interact with the laser beam and a plurality of motors each configured to move at least one of the plurality of optical elements, each of the plurality of motors including an associated encoder configured to measure a position or movement of the motor and to output data representing the measured position or movement; and a controller electrically coupled to the laser beam delivery system including the plurality motors, wherein the controller is configured to: control the laser source and the laser beam delivery system including the plurality of motors based on predefined scan patterns, wherein the laser beam delivery system scans the laser focal spot in the target tissue; while controlling the plurality of motors, receive output data from the plurality of encoders associated with the plurality of motors, and based on the received data, obtain actual motor position data of each of the plurality of motors as a function of time; based on the actual motor position data, and using a pre-stored relationship between actual motor positions and positions of the laser focal spot delivered in the target tissue, calculate a plurality of reconstructed positions of the laser focal spot in the target tissue, wherein the reconstructed positions collectively form a reconstructed geometric representation of an incision in the target tissue; and store or display the reconstructed geometric representation of the incision.

In another aspect, embodiments of the present invention provide a method implemented in an ophthalmic surgical laser system, the ophthalmic surgical laser system including a laser source configured to generate a pulsed laser beam, a laser beam delivery system configured to deliver a laser focal spot of the laser beam to a target tissue of a patient's eye, the laser beam delivery system including a plurality of optical elements each configured to interact with the laser beam and a plurality of motors each configured to move at least one of the plurality of optical elements, each of the plurality of motors including an associated encoder configured to measure a position or movement of the motor and to output data representing the measured position or movement, and a controller electrically coupled to the laser beam delivery system including the plurality motors, the method including, by the controller: controlling the laser source and the laser beam delivery system including the plurality of motors based on predefined scan patterns to scan the laser focal spot in the target tissue; while controlling the plurality of motors, receiving output data from the plurality of encoders associated with the plurality of motors, and based on the received data, obtaining actual motor position data of each of the plurality of motors as a function of time; based on the actual motor position data, and using a pre-stored relationship between actual motor positions and positions of the laser focal spot delivered in the target tissue, calculating a plurality of reconstructed positions of the laser focal spot in the target tissue, wherein the reconstructed positions collectively form a reconstructed geometric representation of an incision in the target tissue; and storing or displaying the reconstructed geometric representation of the incision.

In some embodiments, the plurality of optical elements and the plurality of motors of the ophthalmic surgical laser system include: a high frequency scanner configured to scan the pulsed laser beam back and forth along a fast scan line at a predefined frequency, the fast scan line being centered at a center position and oriented along an orientation; a scan line rotator including a prism or a set of mirrors mounted on a rotating stage which is rotatable around an axis parallel to a propagation direction of the laser beam, and a first motor configured to drive the rotating stage, wherein the scan line rotator is disposed downstream of the high frequency scanner and is configured to rotate the orientation of the fast scan line; an XY scan device including either (1) a focusing lens mounted on an XY scanning stage and a second and a third motor respectively configured to move the XY scanning stage in two orthogonal directions, or (2) two orthogonal scanning mirrors and a second and a third motor respectively configured to rotate the two scanning mirrors, wherein the XY scan device is disposed downstream of the high frequency scanner and is configured to move the center position of the fast scan line in two orthogonal directions perpendicular to the propagation direction of the laser beam; and a Z scan device including a second lens and a fourth motor configured to move the second lens in the propagation direction of the laser beam, wherein the Z scan device is configured to move the center position of the fast scan line in the propagation direction of the laser beam; wherein the step of calculating the plurality of reconstructed positions of the laser focal spot in the target tissue includes: synchronizing the actual motor position data for the first to fourth motors at a common set of time points; for each time point, calculating a reconstructed orientation based on the actual motor position data of the first motor, and calculating a reconstructed center position based on the actual motor position data of the second to fourth motors; and for each time point, based on the reconstructed center position and the reconstructed orientation, generating a plurality of reconstructed positions which form a reconstructed fast scan line centered at the reconstructed center position and oriented along the reconstructed orientation; wherein the reconstructed positions for all of the reconstructed fast scan lines at all of the time points form the reconstructed geometric representation of the incision in the target tissue.

In another aspect, the present invention provides a computer program product comprising a computer usable non-transitory medium (e.g. memory or storage device) having a computer readable program code embedded therein for controlling a data processing apparatus, the computer readable program code configured to cause the data processing apparatus to execute the above method.

It is to be understood that both the foregoing general description and the following detailed description are exemplary and explanatory and are intended to provide further explanation of the invention as claimed.

DETAILED DESCRIPTION OF PREFERRED EMBODIMENTS

Embodiments of this invention relate to systems and methods implemented in an ophthalmic surgical laser system that provide a capability of digitally reconstructing the executed laser cutting pattern, which can aid in system development, manufacturing, service, quality control, and operation, as well as post-op efficacy study.

System Configuration

Figure 1A:
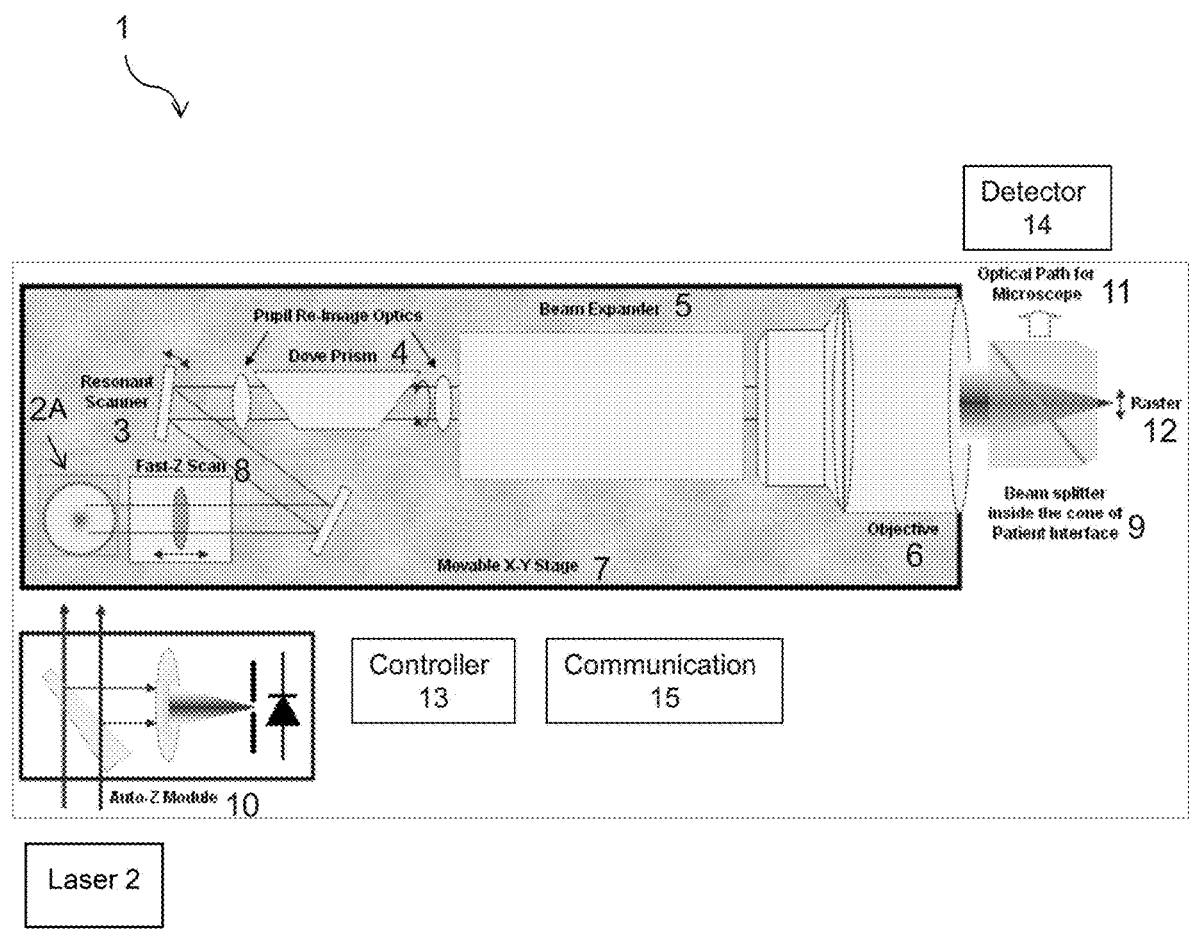
FIGS. 1A and 1B schematically illustrate two exemplary ophthalmic surgical laser systems in which embodiments of the present invention may be implemented.

Referring to the drawings, FIG. 1A shows an ophthalmic surgical laser system 1 suitable for making an incision in a target material such as a cornea of an eye. A laser source 2, such as a femtosecond laser, provides a pulsed laser beam 2A which may be used in optical procedures to treat the eye. The system 1 further includes, but is not limited to, a high frequency scanner (such as a resonant scanner) 3 for scanning the pulsed laser beam to produce a scan line 12 of the pulsed laser beam, a scan line rotator 4 for rotating the scan line 12, a beam expander 5, an objective 6 for focusing the laser beam, an XY scan device 7 for deflecting or directing the laser beam on or within the target, a fast-Z scan device 8, a patient interface 9, an auto-Z device 10, a controller 13, and a communication module 15.

The resonant scanner 3 scans the pulsed laser beam at a high resonant frequency (e.g., thousands of Hz) to produces the scan line that extends in a lateral orientation (i.e. a direction perpendicular to the laser beam propagation direction Z) and having a desired length, for example, between 1 mm and 2 mm. The length of the scan line may be adjustable. The scan line rotator 4 may be implemented by a Dove prism, a Pechan prism, a set of mirrors, or the like, mounted on a rotating stage. By rotating the scan line rotator 4 around the Z axis, the lateral orientation of the scan line 12 is rotated, so that the scan line may be placed at any desired orientation in the XY plane (i.e., the lateral plane perpendicular to the laser beam propagation direction Z). The XY scan device 7 may be a movable XY scanning stage having the focusing objective 6 mounted thereon; the XY scan device 7 carries the objective 6 and moves it relative to the patient interface device 9, so as to move the center of the scan line 12 relative to the patient's eye in the XY directions. The fast-Z scan device 8 changes the depth (i.e. along the Z direction) of the laser focal spot location in the eye. Thus, the scan line rotator 4 modifies the lateral orientation of the scan line 12 while the moveable XY scanning stage 7 and the fast-Z scan device 8 move the center of the scan line in X, Y and Z directions. Because the scanning speed of the resonant scanner is typically much faster than the speed of the XY scanning stage and the fast-Z scan device, the scan line 12 may be referred to as a fast scan line, and the movement of the fast scan line in X, Y and Z directions may be referred to as a slow sweep.

The XY scanning stage 7 may be a motorized stage with two motors that drive its movements in the X and Y directions. Preferably, the XY scanning stage is a recoilless stage configured to reduce or eliminate mechanical vibration. The fast-Z scan device 8 may include a voice coil actuator that drives a lens in the Z direction. Movements of the lens lead to a focus depth change. The z-scan frequency may be between 50 Hz and 15,000 Hz.

The patient interface device 9 couples the patient's eye to the ophthalmic surgical laser system 1. The patient interface 9 may include a visualization beam splitter to reflect the light from the eye along an optical path 11 toward a video microscope or ocular microscope 14, to allow the eye to be imaged by an image detector of the microscope.

The auto Z module 10 measures a distal end surface of a lens of the patient interface coupled to the patient's eye and provides a depth reference for the fast-Z scan device 8 of the ophthalmic laser system. The auto Z module 10 may include, for example, a confocal detector.

The controller 13, which may be implemented by a processor executing suitable machine-readable program code and data stored in a non-volatile memory, is operably coupled to the various components of the system 1 including the laser 2, the fast-Z scan device 8, the resonant scanner 3, the scan line rotator 4, the XY scanning stage 7, the detector 14, and the communication module 15. The controller 13 is configured to direct these components of the system to output the focal spot of the pulsed laser beam in a desired pattern in the eye so as to modify the eye. The communication module 15 provides information to the operator of the laser system 1 at the system and/or remotely via wired or wireless data connection, and may include displays, user input devices such as keyboard, mouse, joystick, etc. The ophthalmic surgical laser system may additionally include an OCT (optical coherence tomography) device (not shown in FIG. 1A, but shown in FIG. 3 as OCT 35) which may be used to measure structures of the target (e.g. eye tissues).

Figure 1B:
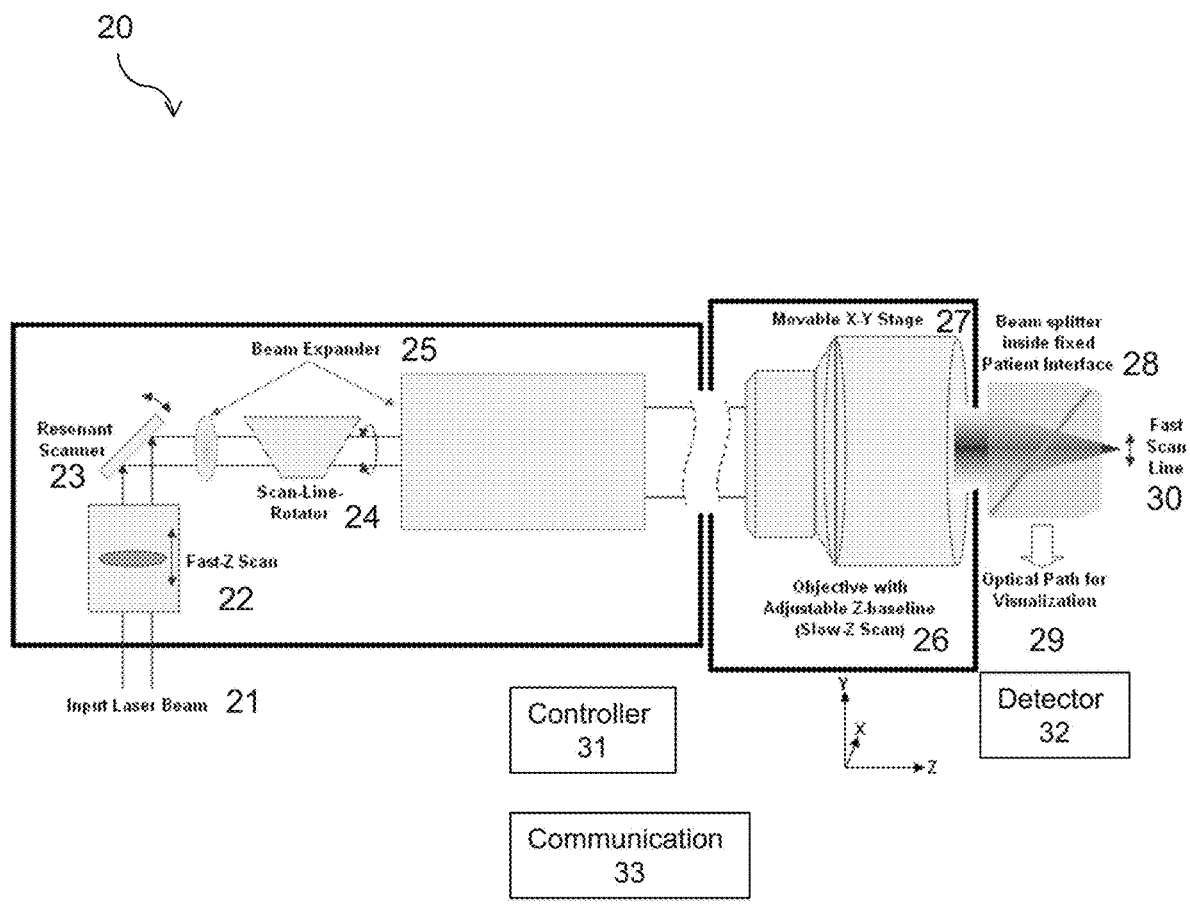

FIG. 1B shows another ophthalmic surgical laser system 20 suitable for making an incision in a target material such as a cornea of an eye. The system 20 includes, but is not limited to, a laser source (not shown) that generates an input pulsed laser beam 21, a fast-Z scan device 22, a resonant scanner 23 for producing a scan line 30 of the pulsed laser beam 21, a scan line rotator 24 for rotating the lateral orientation of the scan line 30, a beam expander 25, an objective with an adjustable focusing mechanism (slow-Z scanner) 26, a XY scanning stage 27 for deflecting or directing the pulsed laser beam 21 on or within the target, a patient interface 28 that may include a beam splitter, a controller 31, an image detector 32 disposed on an optical path 29 defined by the beam splitter of the patient interface, and a communication module 33. The slow-Z scanner 26 may be used to set the laser focal spot at a desired focal depth which may set the Z-baseline of the scan pattern.

One difference between the embodiment of FIG. 1B and that of FIG. 1A is that the XY scanning stage 7 in FIG. 1A carries both the objective 6 and other components including the fast-Z scan device 8, resonant scanner 3, scan line rotator 4, and beam expander 5, while the XY scanning stage 27 in FIG. 1B carries the objective 26 but not the other components mentioned above. Note that the in the system of FIG. 1A, the objective 6 may also be equipped with a slow-Z scanner (also represented by reference symbol 6).

Figure 2A:
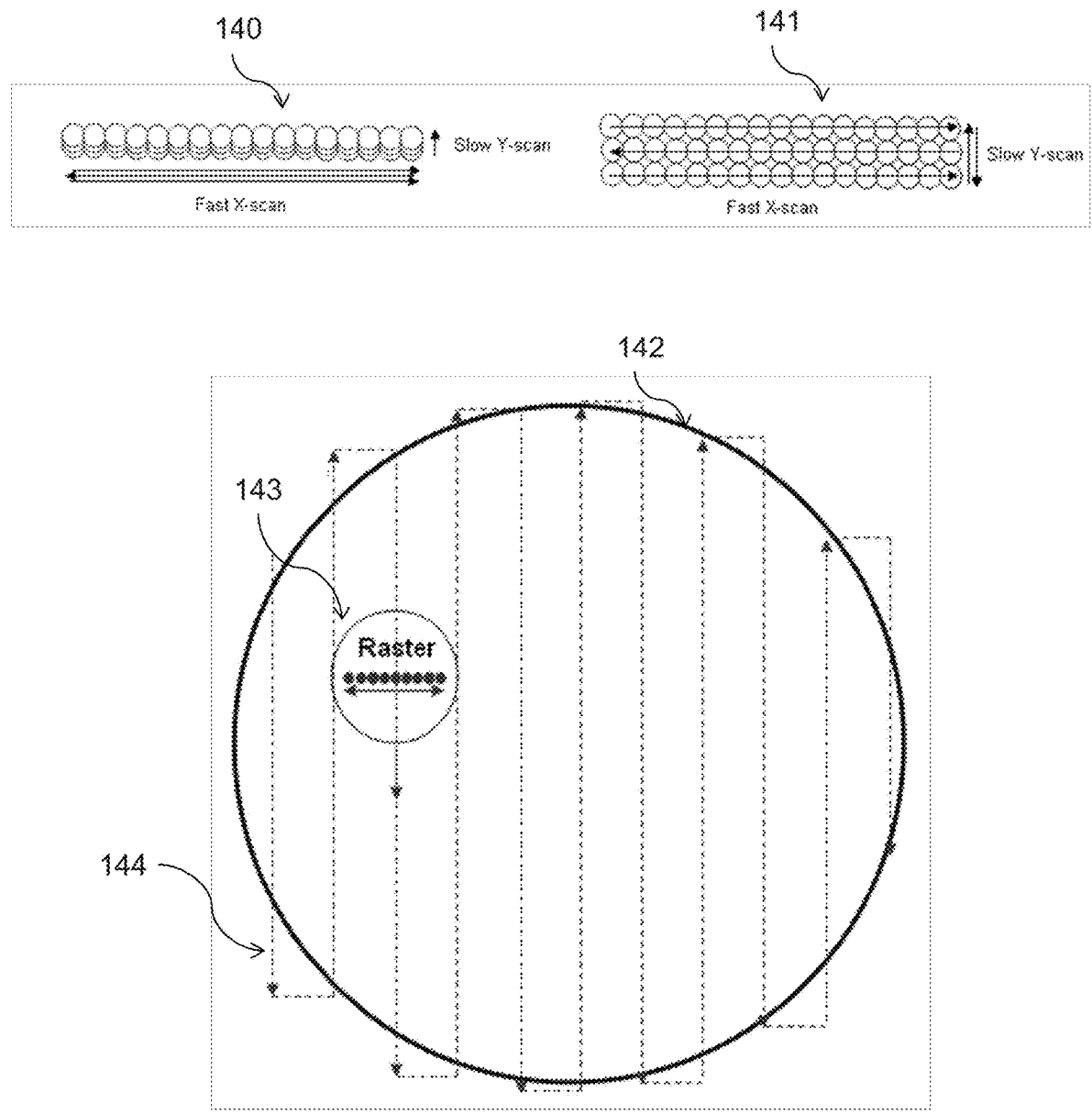
FIGS. 2A-2D schematically illustrate examples of laser scan patterns and corresponding incisions that may be formed using the ophthalmic surgical laser systems of FIGS. 1A and 1B.
Figure 2B:
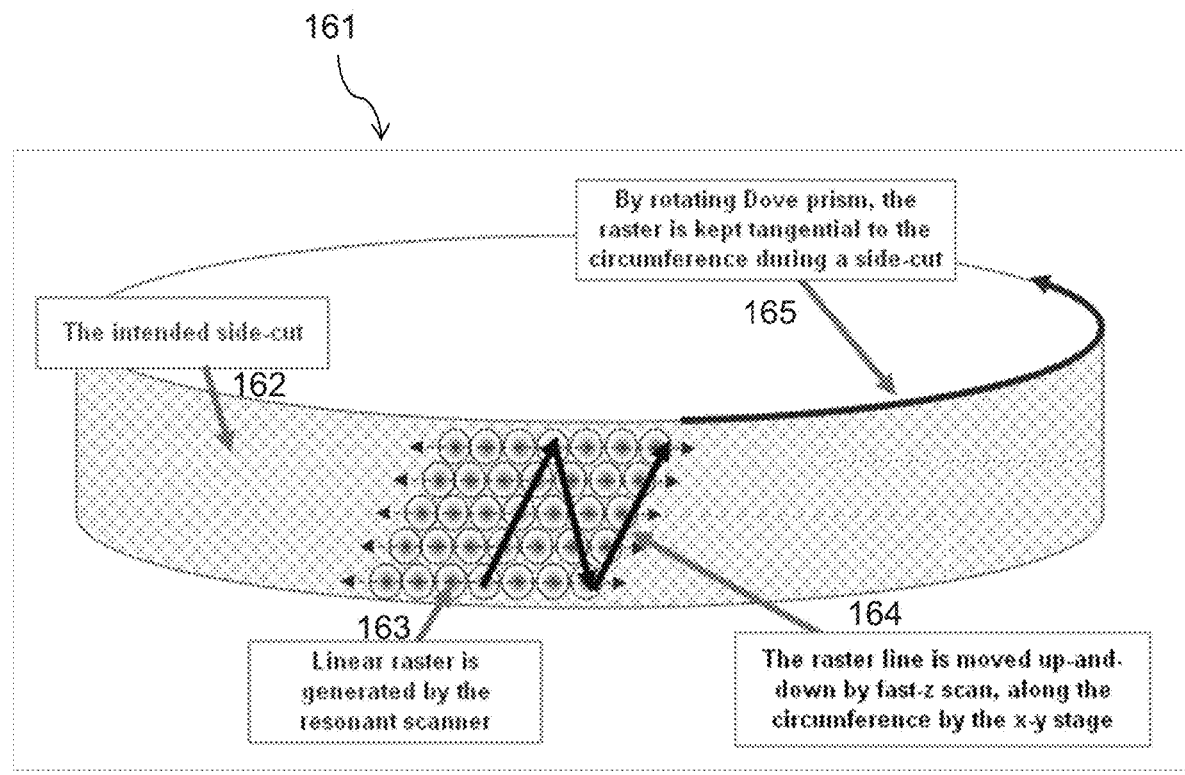
Figure 2C:
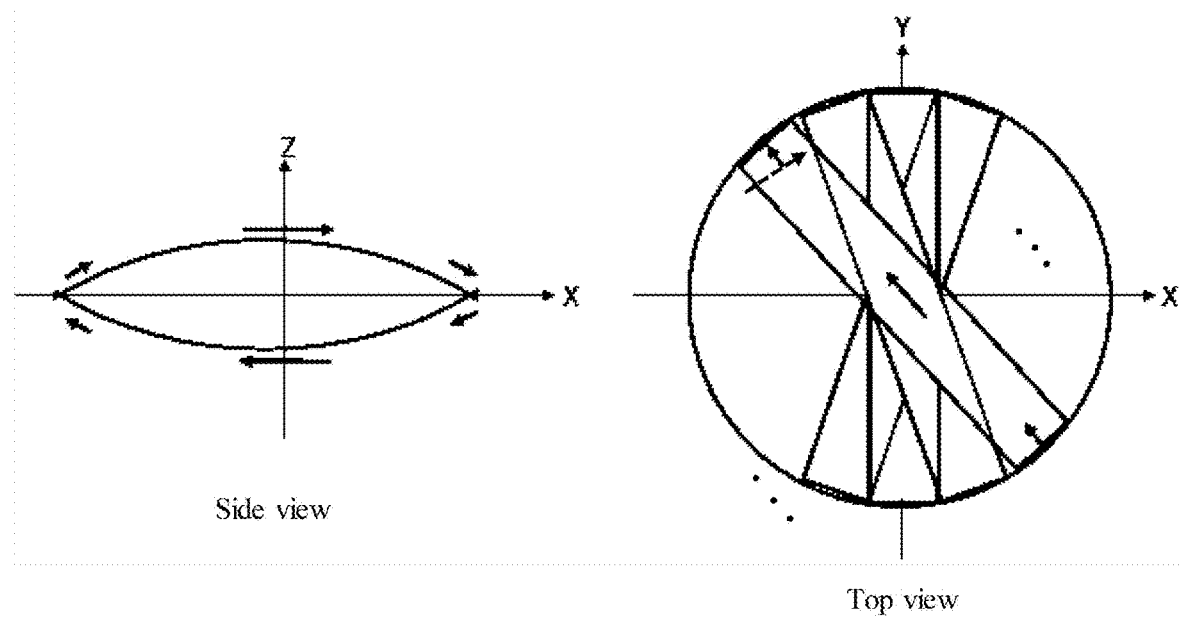

An ophthalmic surgical laser system according to the embodiment of FIG. 1A or FIG. 1B may be used to form incisions of various shapes in the eye. FIGS. 2A, 2B and 2C illustrate three exemplary scan patterns formed by such an ophthalmic surgical laser system. The scan pattern of FIG. 2A forms a planar incision in the XY plane, suitable for forming a bed incision for creating a corneal flap. The fast scan line generated by the resonant scanner (also referred to as a raster line) 143 is maintained at a constant orientation and constant depth in the XY plane, and moved by the XY scanning stage 7 (or 27) across the XY plane. As shown in FIG. 2A, the raster 143 is moved up and down systematically across the surgical field along a serpentine path 144 to form the bed incision approximating a circular shape 142. Raster line scan patterns 140 and 141 illustrate two examples of the fast scan line (extending in the X direction) being moved by the XY scanning stage 7 (or 27) in the Y direction at a speed that is slower compared to the speed of the fast scan in the X direction.

The scan pattern of FIG. 2B forms a cylindrical shape 162 (or a part thereof) extending in the Z direction, suitable for forming a side cut for creating a corneal flap. To form this incision, the raster line 163 generated by the resonant scanner 3 (or 23) is placed along the circumference 165 of the cylinder in a tangential direction. The raster line 163 is moved along a circumference by the X-Y scanning stage 7 (or 27), while a rotation of the scan line by a scan line rotator 4 (or 24) ensures that the raster line is kept tangential to the circumference. Meanwhile, the raster line 163 is moved vertically up and down by the fast-Z scan device 8 (or 22), as indicated by arrows 164, between the top and bottom ends of the cylinder. For example, for a 9.5 mm diameter flap, 20 MHz laser repetition rate, 10 kHz raster scan with 1 mm scan length, an 85 Hz Z-scan frequency and +1-60 µm Z-scan amplitude may be provided. The side-cut may be completed within one second, during which the raster scan passes any given location five times to ensure tissue separation. The side cut need not be vertical and may also be angled to better match the tissue.

Figure 2D:
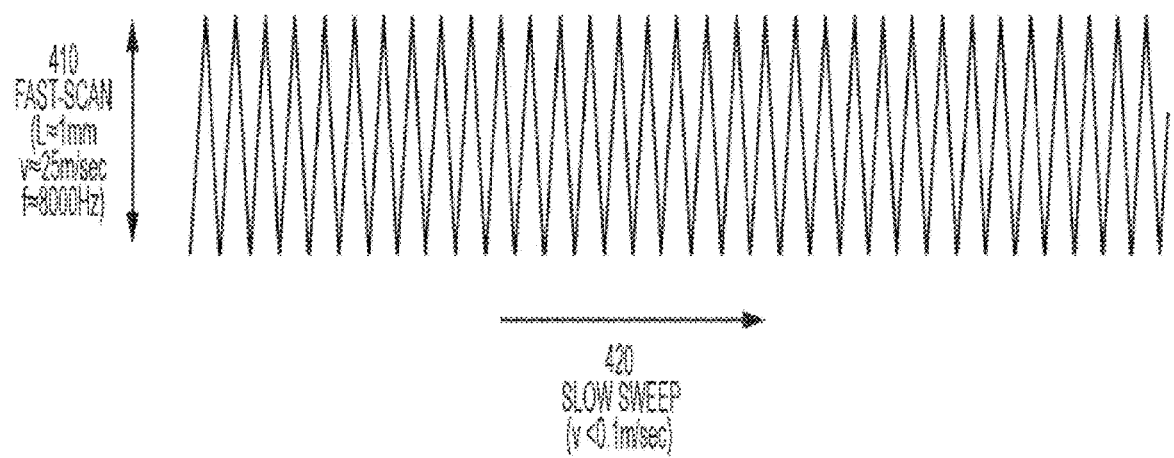

The scan pattern of FIG. 2C forms a top or bottom lenticular incision, each having the shape of a part of a sphere approximately, suitable for forming a lenticular volume in the cornea which can then be extracted to achieve vision correction. Each lenticular incision is formed by a number of sweeps, each sweep (see also FIG. 2D) having a rectangular shape in the top view of the eye (along the Z axis), and an arc shape in the side view which is a part of a circle that passes through the apex of the lenticular surface. To achieve such a scan pattern, the fast scan line is placed tangentially on the circumference of the lenticular surface, and then moved in three dimensions by coordinated motions of the XY scanning stage 7 (or 27) and the fast-Z scan device 8 (or 22), following the arc that passes through the apex of the lenticular surface to the opposite position of the lenticular circumference. The sweep is repeated with the fast scan line located at different starting positions on the circumference, where the orientation of the fast scan line in the top view is rotated by the scan line rotator 4 (or 24) between sweeps. As shown in FIG. 2C, the sweeping speed may be controlled during each sweep so that it is faster near the apex and slower near the circumference.

Further details of ophthalmic surgical laser systems having the configurations shown in FIGS. 1A and 1B are described in commonly owned U.S. patent application Ser. No. 14/970,898, filed Dec. 16, 2015, entitled "Compact Ultra-Short Pulsed Laser Eye Surgery Workstation," and Ser. No. 14/865,396, filed Sep. 25, 2015, entitled "Systems and Methods for Lenticular Laser Incision," which are incorporated herein by reference in their entireties.

In other embodiments, an ophthalmic surgical laser system may employ other types of scanners, such as two orthogonal scanning mirrors, for scanning the laser beam in the transverse (XY) directions. Many such systems are known and their details are not described here.

Figure 3:
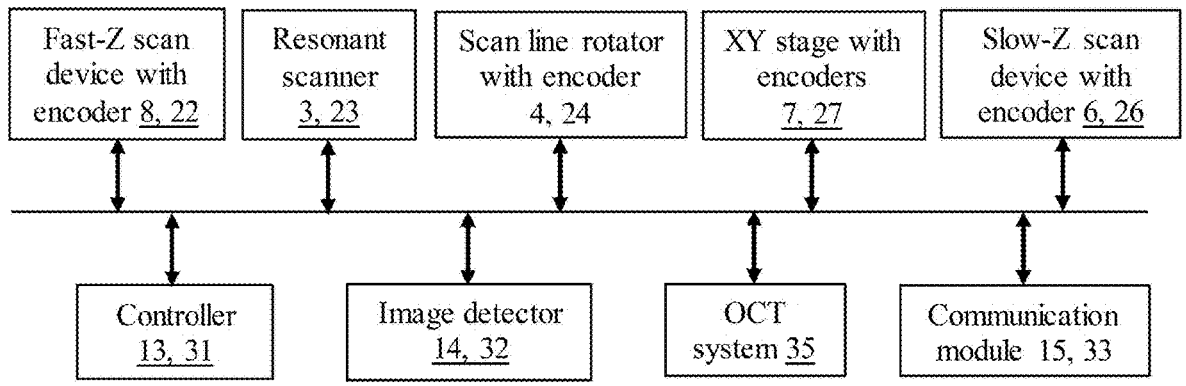
FIG. 3 is a block diagram of a controller and other components of an ophthalmic surgical laser system according to embodiments of the present invention.

In the ophthalmic surgical laser systems shown in FIGS. 1A and 1B, the fast-Z scan device 8, 22, the resonant scanner 3, 23, the scan line rotator 4, 24, the XY scanning stage 7, 27, and slow-Z scanner 6, 26 collectively constitutes the laser beam delivery system which delivers the laser focal spot to the target. These moving components include respective actuators (e.g. linear and/or rotational actuators) which drive their movements. According to embodiments of the present invention, in these moving components, except for the resonant scanner, the actuators are equipped with respective digital encoders (position sensors) to measure and output the positions and/or movements of the actuators as functions of time. The encoders are referred to as digital encoders as they output digital data; the actual mechanisms of measuring the positions and/or movements may by any suitable mechanisms such as optical, magnetic, electrical, etc. Linear and rotational actuators with integrated encoders are commercially available and may be used to implement the embodiments; their structures are known to those skilled in the art, and detailed descriptions are omitted here. The actuators and encoders of the moving components of the system of FIGS. 1A and 1B are electrically coupled to the controller 13, 31, as schematically illustrated in FIG. 3. The controller 13, 31 commands the movements of these moving components, and receives the digital outputs of their respective encoders. Note that if the data from an encoder is movement data, the controller can convert movement to position of the encoder by accumulating the movement data.

The controller controls each actuator (referred to as motor for convenience) of the beam delivery system by transmitting a series of motor commands which contain commanded motor positions and/or movements that are calculated based on an intended scan pattern. However, when the controller commands a series of motor movements during a scan, positional errors between the commanded motor positions and/or movements and the actual positions and/or movements achieved by the motor, referred to as the motor following error, may be present. The motor following error typically has a systematic component and a random component, where the random component is typically smaller than the systematic component. Motor following errors in the various moving components of the laser beam delivery system, whether systematic or random, causes the actual laser focal spot position delivered in the target to deviate from the intended positions as defined by the intended scan pattern, causing the actual achieved laser scan pattern to be less than ideal.

According to embodiments of the present invention, during the execution of a laser treatment scan, the actual positions of the various motors of the beam delivery system are measured by the corresponding encoders and recorded. Based on the recorded actual motor positions, the positions of the laser focal spot delivered in the eye tissue are calculated to digitally reconstruct the laser cutting patterns formed by the laser focal spots. The digitally reconstructed laser cutting patterns may then be analyzed for various purposes, such as for analyzing cutting errors and refractive performance, for trouble-shooting, as a scanning quality inspector, as a data archive for the treatment execution, etc., as will be described in more detail later.

Figure 4:
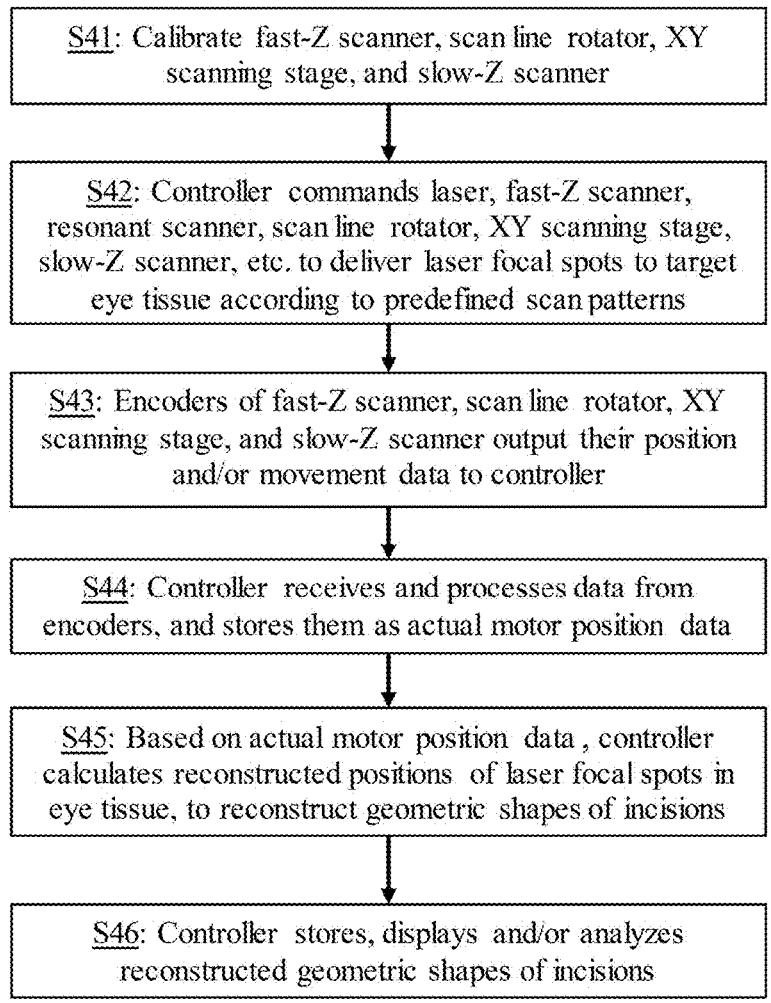
FIGS. 4 and 5 are flowcharts illustrating a laser cutting pattern reconstruction method according to an embodiment of the present invention.

A laser treatment and laser cutting patterns reconstruction method according to embodiments of the present invention is described with reference to FIGS. 4 and 5.

Prior to executing laser treatment scans, the various moving components of the laser beam delivery system, including the fast-Z scanner, the scan line rotator, the XY scanning stage, and the slow-Z scanner, are calibrated (step S41). The calibration process establishes the relationship between the commanded motor positions of the various moving components and the laser focal spot positions in the target, as well as the relationship between the actual motor positions of the moving components (as measured by the encoders) and the laser focal spot positions in the target. These relationships may be stored, for example, as lookup tables in the memory. Calibration may be performed for a given surgical laser system from time to time. Some of the calibration steps, such z direction calibration that establishes the relationship between the fast and slow-Z scanners and the distal surface of the patient interface device, may be performed each time before treating a patient.

In ophthalmic surgical laser system where the moving components of the laser beam delivery system are not equipped with encoders, calibration processes are performed to establish the relationship between the commanded motor positions and the laser focal spot positions in the target. The calibration process may involve using an artificial target, such as a calibration plate which may reflect or transmit the laser beam, a fluorescent block which may generate fluorescent light when illuminated by the laser beam, a calibration gel or viscoelastic fluid which may form a mark when illuminated by the laser beam, a glass coverslip which may reflect or otherwise interact with the laser beam, etc., and measuring signals generated from the artificial target in response to the pulsed laser beam. The signals are typically optical signals and are detected using the image detector, the OCT device, and/or other detectors of the ophthalmic surgical laser system. The measured signal positions are correlated with the commanded motor positions to establish their relationship. Examples of laser system calibration methods are described in, for example, U.S. patent application Ser. No. 14/666,743, filed Mar. 24, 2015, entitled "Automated Calibration of Laser System and Tomography System with Fluorescent Imaging of Scan Pattern;" Ser. No. 14/509,850, filed Oct. 8, 2014, entitled "Laser Eye Surgery System Calibration;" and Ser. No. 16/112,507, filed Aug. 24, 2018, entitled "Detection of Optical Surface of Patient Interface for Ophthalmic Laser Applications Using a Non-Confocal Configuration."

In embodiments of the present invention, the conventional calibration methods are expanded to also establish the relationship between the actual motor positions (as measured by the corresponding encoders) and the laser focal spot positions measured from the target. More specifically, the calibration step includes commanding the motors to move to respective commanded motor positions, measuring the actual motor positions by the encoders, and measuring the laser focal spot position in the target; repeating the above steps for a plurality of different commanded positions. The commanded motor positions, the actual motor positions, and the measured laser focal spot positions in the target are correlated with each other in this manner. As mentioned earlier, due to motor following errors, the actual motor positions often deviate from the commanded motor positions, and the motor following errors may have both systematic and random components.

When executing a treatment scan, the controller commands the laser, the fast-Z scanner, the resonant scanner, the scan line rotator, the XY scanning stage, and the slow-Z scanner, as well as other relevant components of the ophthalmic surgical laser system, to deliver the focal spot of the pulsed laser beam to the target eye tissue according to predefined scan patters to perform an incision in the eye tissue (step S42). The commanded motor positions and/or movements in the motor commands are calculated based on the scan patterns and the intended incision shapes, such as, without limitation, those shown in FIGS. 2A-2C. For example, as described earlier, to form a top or bottom lenticular shaped incision, the scan pattern includes a plurality of curved sweeps where the fast scan line is moved along an arc.

While the various components execute the commands to scan the laser focal spot in the eye tissue, the respective encoders of the fast-Z scanner, the scan line rotator, the XY scanning stage, and the slow-Z scanner output the positions and/or movements data to the controller (step S43). Note that the encoder data from the slow-Z scanner is optional, as some scan patterns may not involve movements of the slow-Z scanner, and some laser systems do not have a slow-Z scanner. The controller receives the outputs of the encoders, converts movement data to position data if needed, and stores them as actual motor position data in the memory (step S44). Each piece of actual motor position data is associated with a time stamp, which may be generated either by the encoders themselves or by the controller.

From the actual motor position data, and using the calibration relationship between the actual motor positions as measured by the encoders and the laser focal spot positions in the target established in step S41, the controller calculates the positions of the laser focal spot in the eye tissue that correspond to the actual motor positions (step S45). The calculated positions of the laser focal spot, referred to as reconstructed positions, are deemed to accurately represent the actual positions of the laser focal spot delivered in the eye tissue during the scan. The collection of the reconstructed laser focal spot positions form a reconstructed geometric shape, which is deemed to be an accurate representation of the laser cutting pattern actually formed in the tissue by the scan.

Note that even though a reconstruction can also be calculated from the commanded motor positions, due to motor following errors that may have occurred during the scan, such a reconstruction may not be an accurate representation of the laser cutting pattern actually formed in the tissue by the scan.

Figure 5:
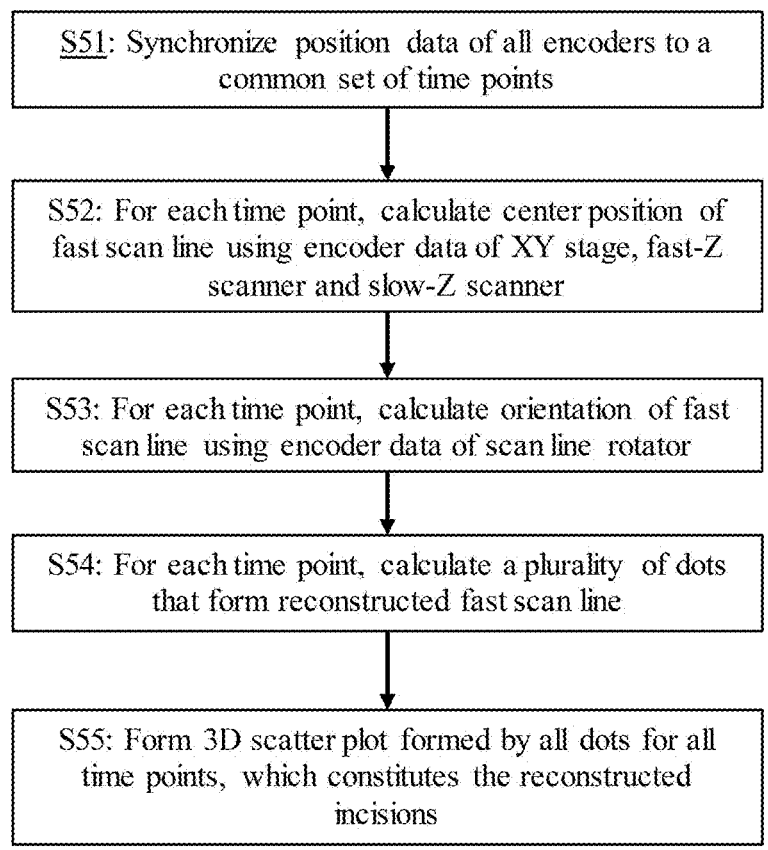

Referring to FIG. 5, in an ophthalmic surgical laser system such that shown in FIG. 1A or 1B, the step of calculating the laser focal spot positions and digitally reconstructing geometric shape of laser cutting patterns may be performed as follows. The position data of all encoders are synchronized (step S51). In other words, if the time stamps of data points of different encoders are staggered, the controller calculates the encoder positions of all encoders at a common set of time points during the scan, e.g. by interpolating the data from each individual encoder. For each time point, the encoder data of the XY scanning stage, the fast-Z scanner and the slow-Z scanner (if any) are used to calculate a position within the target eye tissue, which represents the center of the fast scan line to be reconstructed (step S52), and the encoder data of the scan line rotator is used to calculate the orientation of the fast scan line to be reconstructed (step S53). These calculations are based on the calibration relationship, using interpolation as needed. For each time point, based on the fast scan line center position and orientation, and other scan parameters such as the scan line length, a plurality of dots are calculated to form the reconstructed fast scan line (step S54). Each dot may be in the form of a sphere having a predefined diameter. The 3-dimensional scatter plot formed by the collection of these dots for all time points constitutes the reconstructed laser cutting pattern (step S55), which may be displayed for visual inspection and/or stored for further analyses (step S46). In preferred embodiments, when generating the 3D scatter plot, the dots are not fitted to any analytical surface.

In preferred embodiments, when performing the reconstruction, certain measures are taken to reduce the amount of data of the calculation. First, when forming the dots for each reconstructed fast scan line in step S54, the number of dots per fast scan line is preferably smaller than the actual number of laser pulses per fast scan line delivered during the scan. For example, the actual scan may have 600 laser pulses per fast scan line (which is determined by the laser pulse repetition rate and the frequency of the resonant scanner), while only 60 dots per fast scan line are generated for the reconstruction. Second, the number of fast scan lines (i.e. the number of time points) used to form the reconstruction is preferably smaller than the actual number of fast scan lines delivered during the scan. For example, the actual scan may have 16 fast scan lines per ms (which is determined by the frequency of the resonant scanner), while only 1 fast scan lines per ms is generated for the reconstruction (i.e. 1 time point per ms). This results in a 10 fold data reduction per fast scan line and a 16 fold data reduction in the moving direction of the fast scan line. Each dot in the reconstruction is in the form of a sphere of approximately 5 µm in diameter (or more generally, of 4-6 µm in diameter). This is slightly larger than the actual bubbles formed by the laser pulses in the eye tissue, which are typically about 3 µm in diameter. In the actual scan, the bubbles overlap each other in order to physically separate the tissue. In the reconstruction, the spheres will be in close proximity with each other, e.g., they may overlap each other slightly, or are separated from each other by a distance on the same order of magnitude as their diameter, after the reduction in spatial density described above. Such spatial density reduction gives satisfactory reconstructions, where each reconstructed surface may contain billions of spheres. In practice, data reduction is important for achieving satisfactory calculation speed. In some embodiments, the use may select or change parameters used in the reconstruction calculation, such as the spatial density and the size of the spheres.

Figure 6A:
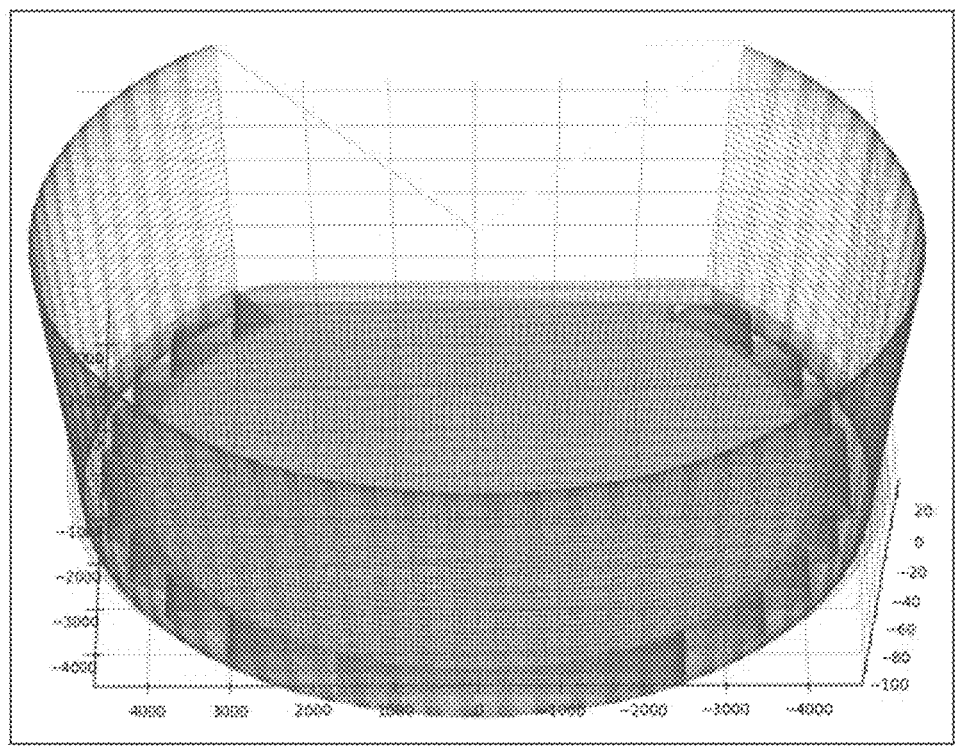
FIGS. 6A and 6B show two examples of reconstructed laser cutting patterns using the laser cutting pattern reconstruction method.
Figure 6B:
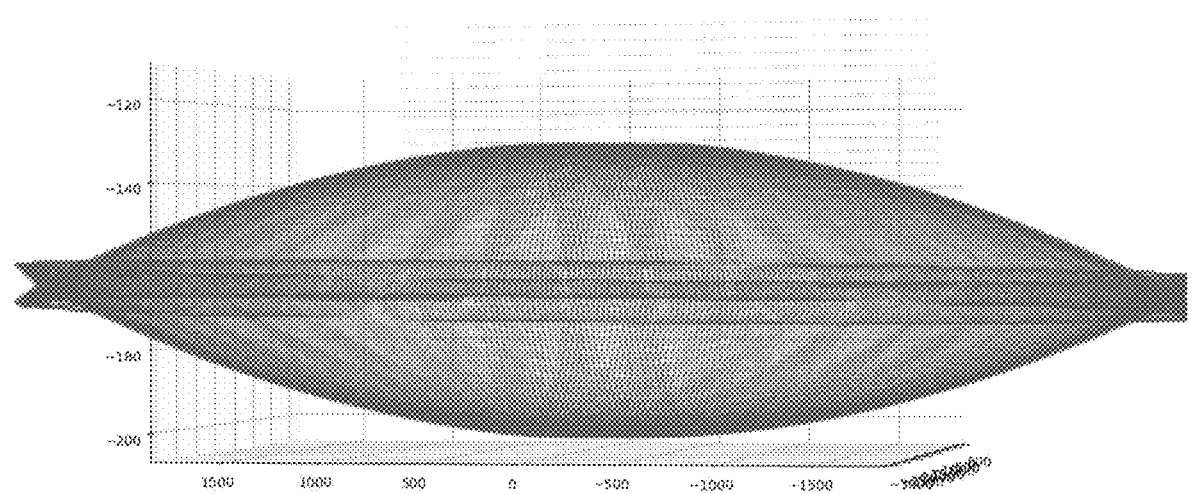

FIGS. 6A and 6B show two exemplary reconstructed laser cutting patterns, namely a flap pattern and a lenticule pattern, respectively, based on measured motor position data using the reconstruction method described above.

As mentioned earlier, because the reconstruction is generated from the encoder data which represent the actual motors positions during the laser scan, it accurately represents the shape of the laser cutting pattern that was actually formed in the eye tissue by the scan. Also as mentioned earlier, due to motor following error, the actual laser focal spot position delivered in the target may deviate from the intended positions as defined by the intended scan pattern. Therefore, the reconstruction allows the user to analyze the reconstructed incision shape to evaluate the performance of the ophthalmic procedure. Additional software may be provided to perform such analyses.

In one example (cutting error analyzer), the differences between the reconstructed shapes and the intended shapes may be analyzed and reported. For example, for a flap procedure, the user may calculate the flap thickness, diameter, side angle, hinge position, and hinge angle, etc. from the reconstruction and compare them with the intended values.

In another example (refractive performance analyzer), for a corneal lenticule procedure, the lenticule shape may be reconstructed, and the corresponding refractive correction can be evaluated. For example, the reconstructed lenticule shape may be fitted to a set of Zernike polynomials (or other suitable polynomial functions) to calculate both low order and high order refractive corrections of the actual incisions. This is particularly important when estimating high order aberrations, because even sub-micron errors in the incisions may cause significant error in the high order refractive corrections. The analysis can provide reliable evaluation of high order aberrations, allowing the user to confirm that the high order correction is being executed correctly.

The reconstructed laser cutting patterns, after the dots are fitted to curves, may also be used with commercially available optical design software, such as OpticStudio, to analyze the cutting results using ray tracing.

The reconstructed laser cutting patterns may also be used with corneal bio-mechanic finite element analysis models to evaluate the impact of the cutting on cornea bio-mechanics, for example, to simulate tissue resettling and healing. Corneal bio-mechanical models are generally known to those skilled in the relevant art.

In practice, the laser cutting pattern reconstruction method may be used as a trouble-shooting tool for tissue incision issues. For example, the reconstructed laser cutting patterns can explicitly show which cut segment did not go as intended, or even the intended pattern was wrong. The reconstruction method may serve as a scanning quality inspector. For example, by using reconstructed laser cutting patterns, one may grade the performance of the cutting pattern, for different cutting segments, and/or for the whole cutting pattern. A quality score may be constructed, by taking into consideration the magnitude of the error in the reconstructed cutting pattern combined with the criticality of where the error occurs, which may be used as a test criteria for the scanning system. The reconstruction method may also serve as a data archive for the treatment execution. This may be particularly important for certain types of treatment, such as corneal lenticule vision correction. With the reconstructed laser cutting patterns, the exact cut pattern that has been executed during each treatment is recorded. This may aid in understanding the relationship between the exact surgical cuts and the treatment outcome, which may further help the design and refinement of various aspects of the treatment procedure.

While the laser beam delivery systems in the above described embodiments employ a resonant scanner, scan line rotator, and XY and Z scanners, the laser cutting pattern reconstruction method described above is applicable to ophthalmic surgical laser systems where the laser beam delivery systems employ other types of optical structures to scan the laser beam in the target tissue. For example, the laser beam delivery systems may employ two rotating mirrors or other optics to angularly deflect and scan the pulsed laser beam in the X and Y directions, without using a resonant scanner or scan line rotator. More generally, the laser cutting pattern reconstruction method described above is applicable to any ophthalmic surgical laser system where the laser beam delivery system includes a plurality of moving components, each moving component including at least one optical element (e.g., scanner, prism, mirror, lens, etc.) that interacts with the laser beam and at least one motor to move the optical element, where each motor is equipped with an encoder to sense the position and/or movement of the motor and to output the sensed data to the controller. Those of ordinary skill in the art can readily modify the method steps described above with reference to FIGS. 4 and 5 to adapt them to any ophthalmic surgical laser system.

Further, the controller of the ophthalmic surgical laser system may employ a distributed computing system, where parts of it may control the moving components and other components of the ophthalmic surgical laser system and parts of it may perform the reconstruction process and/or subsequent analyses of the reconstructed laser cutting patterns.

While certain illustrated embodiments of this disclosure have been shown and described in an exemplary form with a certain degree of particularity, those skilled in the art will understand that the embodiments are provided by way of example only, and that various variations can be made without departing from the spirit or scope of the invention. Thus, it is intended that this disclosure cover all modifications, alternative constructions, changes, substitutions, variations, as well as the combinations and arrangements of parts, structures, and steps that come within the spirit and scope of the invention as generally expressed by the following claims and their equivalents.

What is claimed is:

1. An ophthalmic surgical laser system comprising:
   a laser source configured to generate a pulsed laser beam;
   a laser beam delivery system configured to deliver a laser focal spot of the laser beam to a target tissue of a patient's eye, the laser beam delivery system including a plurality of optical elements each configured to interact with the laser beam and a plurality of motors each configured to move at least one of the plurality of optical elements, each of the plurality of motors including an associated encoder configured to measure a position or movement of the motor and to output data representing the measured position or movement; and
   a controller electrically coupled to the laser beam delivery system including the plurality motors, wherein the controller is configured to:
      control the laser source and the laser beam delivery system including the plurality of motors based on predefined scan patterns, wherein the laser beam delivery system scans the laser focal spot in the target tissue;
      while controlling the plurality of motors, receive output data from the plurality of encoders associated with the plurality of motors, and based on the received data, obtain actual motor position data of each of the plurality of motors as a function of time;
      based on the actual motor position data, and using a pre-stored relationship between actual motor positions and positions of the laser focal spot delivered in the target tissue, calculate a plurality of reconstructed positions of the laser focal spot in the target tissue, wherein the reconstructed positions collectively form a reconstructed geometric representation of an incision in the target tissue; and
      store or display the reconstructed geometric representation of the incision.

2. The ophthalmic surgical laser system of claim 1, wherein the plurality of optical elements and the plurality of motors include:
   a high frequency scanner configured to scan the pulsed laser beam back and forth along a fast scan line at a predefined frequency, the fast scan line being centered at a center position and oriented along an orientation;
   a scan line rotator including a prism or a set of mirrors mounted on a rotating stage which is rotatable around an axis parallel to a propagation direction of the laser beam, and a first motor configured to drive the rotating stage, wherein the scan line rotator is disposed downstream of the high frequency scanner and is configured to rotate the orientation of the fast scan line;

an XY scan device including either (1) a focusing lens mounted on an XY scanning stage and a second and a third motor respectively configured to move the XY scanning stage in two orthogonal directions, or (2) two orthogonal scanning mirrors and a second and a third motor respectively configured to rotate the two scanning mirrors, wherein the XY scan device is disposed downstream of the high frequency scanner and is configured to move the center position of the fast scan line in two orthogonal directions perpendicular to the propagation direction of the laser beam; and a Z scan device including a second lens and a fourth motor configured to move the second lens in the propagation direction of the laser beam, wherein the Z scan device is configured to move the center position of the fast scan line in the propagation direction of the laser beam.

3. The ophthalmic surgical laser system of claim 2, wherein the controller is configured to calculate the plurality of reconstructed positions of the laser focal spot in the target tissue by:

synchronizing the actual motor position data for the first to fourth motors at a common set of time points;

for each time point, calculating a reconstructed orientation based on the actual motor position data of the first motor, and calculating a reconstructed center position based on the actual motor position data of the second to fourth motors; and for each time point, based on the reconstructed center position and the reconstructed orientation, generating a plurality of reconstructed positions which form a reconstructed fast scan line centered at the reconstructed center position and oriented along the reconstructed orientation;

wherein the reconstructed positions for all of the reconstructed fast scan lines at all of the time points form the reconstructed geometric representation of the incision in the target tissue.

4. The ophthalmic surgical laser system of claim 3, wherein the controller is configured to control the laser source and the high frequency scanner to scan a first number of laser pulses in each fast scan line; and wherein the controller is configured to, when calculating the plurality of reconstructed positions, generate a second number of reconstructed positions along each reconstructed fast scan line, wherein the second number is smaller than the first number.

5. The ophthalmic surgical laser system of claim 4, wherein the controller is configured to control the high frequency scanner to form a third number of fast scan lines per unit time; and wherein the controller is configured to, when calculating the plurality of reconstructed positions, generate a fourth number of reconstructed fast scan lines per unit time, wherein the fourth number is smaller than the third number.

6. The ophthalmic surgical laser system of claim 1, further comprising an imaging system electrically coupled to the controller, wherein the controlled is configured to generate the relationship between actual motor positions and positions of the laser focal spot delivered in the target tissue by:

controlling the laser source and the laser beam delivery system including the plurality of motors to deliver the laser focal spot to a plurality of positions in an artificial target;

controlling the imaging system to measure each of the plurality of positions of the laser focal spots in the artificial target;

while controlling the plurality of motors, receiving output data from the plurality of encoders associated with the plurality of motors, and based on the received data, obtaining actual motor position data of each of the plurality of motors corresponding to each of the plurality of positions; and generating the relationship by associating the actual motor positions data with the measured positions of the laser focal spot in the artificial target.

7. The ophthalmic surgical laser system of claim 1, wherein the controller is further configured to compare the reconstructed geometric representation of the incision with the predefined scan patterns.

8. The ophthalmic surgical laser system of claim 1, wherein the controller is further configured to calculate a refractive correction associated with the reconstructed geometric representation of the incision by fitting the reconstructed geometric representation to a set of polynomial functions.

9. The ophthalmic surgical laser system of claim 1, wherein the controller is further configured to simulate tissue resettling based on the reconstructed geometric representation of the incision and a tissue bio-mechanic finite element analysis model.

10. A method implemented in an ophthalmic surgical laser system, the ophthalmic surgical laser system including a laser source configured to generate a pulsed laser beam, a laser beam delivery system configured to deliver a laser focal spot of the laser beam to a target tissue of a patient's eye, the laser beam delivery system including a plurality of optical elements each configured to interact with the laser beam and a plurality of motors each configured to move at least one of the plurality of optical elements, each of the plurality of motors including an associated encoder configured to measure a position or movement of the motor and to output data representing the measured position or movement, and a controller electrically coupled to the laser beam delivery system including the plurality motors, the method comprising, by the controller:

controlling the laser source and the laser beam delivery system including the plurality of motors based on predefined scan patterns to scan the laser focal spot in the target tissue;

while controlling the plurality of motors, receiving output data from the plurality of encoders associated with the plurality of motors, and based on the received data, obtaining actual motor position data of each of the plurality of motors as a function of time;

based on the actual motor position data, and using a pre-stored relationship between actual motor positions and positions of the laser focal spot delivered in the target tissue, calculating a plurality of reconstructed positions of the laser focal spot in the target tissue, wherein the reconstructed positions collectively form a reconstructed geometric representation of an incision in the target tissue; and storing or displaying the reconstructed geometric representation of the incision.

11. The method of claim 10, wherein the plurality of optical elements and the plurality of motors of the ophthalmic surgical laser system include:
- a high frequency scanner configured to scan the pulsed laser beam back and forth along a fast scan line at a predefined frequency, the fast scan line being centered at a center position and oriented along an orientation;
- a scan line rotator including a prism or a set of mirrors mounted on a rotating stage which is rotatable around an axis parallel to a propagation direction of the laser beam, and a first motor configured to drive the rotating stage, wherein the scan line rotator is disposed downstream of the high frequency scanner and is configured to rotate the orientation of the fast scan line;
- an XY scan device including either (1) a focusing lens mounted on an XY scanning stage and a second and a third motor respectively configured to move the XY scanning stage in two orthogonal directions, or (2) two orthogonal scanning mirrors and a second and a third motor respectively configured to rotate the two scanning mirrors, wherein the XY scan device is disposed downstream of the high frequency scanner and is configured to move the center position of the fast scan line in two orthogonal directions perpendicular to the propagation direction of the laser beam; and
- a Z scan device including a second lens and a fourth motor configured to move the second lens in the propagation direction of the laser beam, wherein the Z scan device is configured to move the center position of the fast scan line in the propagation direction of the laser beam;

wherein the step of calculating the plurality of reconstructed positions of the laser focal spot in the target tissue includes:
- synchronizing the actual motor position data for the first to fourth motors at a common set of time points;
- for each time point, calculating a reconstructed orientation based on the actual motor position data of the first motor, and calculating a reconstructed center position based on the actual motor position data of the second to fourth motors; and
- for each time point, based on the reconstructed center position and the reconstructed orientation, generating a plurality of reconstructed positions which form a reconstructed fast scan line centered at the reconstructed center position and oriented along the reconstructed orientation;
- wherein the reconstructed positions for all of the reconstructed fast scan lines at all of the time points form the reconstructed geometric representation of the incision in the target tissue.

12. The method of claim 11,
wherein the step of controlling the laser source and the laser beam delivery system includes controlling the laser source and the high frequency scanner to scan a first number of laser pulses in each fast scan line; and
wherein the step of calculating the plurality of reconstructed positions includes generating a second number of reconstructed positions along each reconstructed fast scan line, wherein the second number is smaller than the first number.

13. The method of claim 12,
wherein the step of controlling the laser source and the laser beam delivery system includes controlling the high frequency scanner to form a third number of fast scan lines per unit time; and
wherein the step of calculating the plurality of reconstructed positions includes generating a fourth number of reconstructed fast scan lines per unit time, wherein the fourth number is smaller than the third number.

14. The method of claim 10, wherein the ophthalmic surgical laser system further includes an imaging system electrically coupled to the controller, the method further comprising generating the relationship between actual motor positions and positions of the laser focal spot delivered in the target tissue, including, by the controller:
- controlling the laser source and the laser beam delivery system including the plurality of motors to deliver the laser focal spot to a plurality of positions in an artificial target;
- controlling the imaging system to measure each of the plurality of positions of the laser focal spots in the artificial target;
- while controlling the plurality of motors, receiving output data from the plurality of encoders associated with the plurality of motors, and based on the received data, obtaining actual motor position data of each of the plurality of motors corresponding to each of the plurality of positions; and
- generating the relationship by associating the actual motor positions data with the measured positions of the laser focal spot in the artificial target.

15. The method of claim 10, further comprising, by the controller, comparing the reconstructed geometric representation of the incision with the predefined scan patterns.

16. The method of claim 10, further comprising, by the controller, calculating a refractive correction associated with the reconstructed geometric representation of the incision by fitting the reconstructed geometric representation to a set of polynomial functions.

17. The method of claim 10, further comprising, by the controller, simulating tissue resettling based on the reconstructed geometric representation of the incision and a tissue bio-mechanic finite element analysis model.

* * * * *